United States Patent
Nishiyama et al.

(10) Patent No.: US 7,906,760 B2
(45) Date of Patent: Mar. 15, 2011

(54) INSPECTION METHOD AND REAGENT SOLUTION

(75) Inventors: Hidetoshi Nishiyama, Tokyo (JP); Mitsuo Suga, Saitama (JP); Mitsuru Koizumi, Tokyo (JP)

(73) Assignee: JEOL Ltd., Tokyo (JP)

( * ) Notice: Subject to any disclaimer, the term of this patent is extended or adjusted under 35 U.S.C. 154(b) by 235 days.

(21) Appl. No.: 12/335,143

(22) Filed: Dec. 15, 2008

(65) Prior Publication Data
US 2009/0250609 A1    Oct. 8, 2009

(30) Foreign Application Priority Data
Apr. 8, 2008    (JP) .................... 2008-099856

(51) Int. Cl.
*H01J 37/20*    (2006.01)
(52) U.S. Cl. ..... 250/307; 250/310; 250/311; 250/442.11
(58) Field of Classification Search .................. 250/307, 250/306, 310, 311, 442.11
See application file for complete search history.

(56) References Cited

U.S. PATENT DOCUMENTS 5,498,550 A * 3/1996 Fujiwara et al. ............. 436/526
6,777,674 B2 * 8/2004 Moore et al. ...................... 850/9

FOREIGN PATENT DOCUMENTS

| JP | 47-24961 A | 10/1972 |
| JP | 06-318445 A | 11/1994 |
| JP | 2004-515049 T | 5/2004 |
| JP | 2007-292702 A | 11/2007 |

OTHER PUBLICATIONS

Green, Evan Drake Harriman, PH.D., Chapter 1, Introduction, Atmospheric scanning electron microscopy, Stanford University, 1993, pp. 1-12.

* cited by examiner

*Primary Examiner* — Kiet T Nguyen
(74) *Attorney, Agent, or Firm* — The Webb Law Firm (57) ABSTRACT

An electron microscope method for inspecting a liquid specimen and a reagent solution therefor. A culture medium and biological cells are put in the sample holder. A plugging agent is mixed into the liquid sample. The cells can be irradiated with a primary beam via a film. An image of the cells or information about the cells is obtained by detecting a resulting secondary signal. If the film is destroyed, the plugging agent plugs up the damaged portion of the film. Consequently, liquid leakage can be minimized.

11 Claims, 4 Drawing Sheets

INSPECTION METHOD AND REAGENT SOLUTION

BACKGROUND OF THE INVENTION

1. Field of the Invention

The present invention relates to an inspection method permitting efficient observation or inspection of a liquid sample containing cultured cells or the like. The invention also relates to a reagent solution used in this inspection method.

2. Description of Related Art

Living organisms including human beings are multicellular animals. Living organisms develop diseases if information cannot be transmitted normally among cells or if viruses or chemical substances cling to cells. For this reason, in the fields of molecular biology and pharmaceutics, research is conducted by peeling off cells from a living organism, cultivating the cells on a laboratory dish, giving a stimulus, such as electricity, chemical substance, or medicine to the cells, and observing the resulting reaction on the cellular level.

In the past, optical microscopes have been used for such observation. Manipulators or pipettes have been employed to give stimuli to cells. Frequently, important portions to be observed are very tiny regions of less than 0.1 µm that are impossible to observe with an optical microscope. For example, diseases arising from the inability to exchange substances normally among biological cells include hypertension, diabetes insipidus, arrhythmia, myopathy, diabetes, and deprementia. Exchange of substances among cells is performed by ion channels having sizes of about 10 nm existing in cell membranes. Because it is difficult to observe such ion channels with optical microscopes, there has been a demand for a technique enabling observation using a scanning electron microscope (SEM) having high resolution.

However, a sample to be inspected with an inspection apparatus incorporating SEM capabilities is normally placed in a sample chamber whose inside pressure has been reduced by vacuum pumping. The sample placed in the sample chamber, which, in turn, is placed in a reduced-pressure ambient in this way, is irradiated with an electron beam (charged-particle beam). Secondary signals, such as secondary electrons or backscattered electrons, produced from the sample in response to the irradiation are detected.

In such inspection of a sample using SEM, the sample is exposed to a reduced-pressure ambient. Therefore, moisture evaporates from the sample, so that the cells die. It has been impossible to observe reactions of living cells to a stimulus.

Accordingly, when an inspection is performed under the condition where the sample contains moisture, it is necessary to prevent the sample from being exposed to the reduced-pressure ambient; otherwise, moisture would evaporate from the sample. One conceivable method of inspecting a sample using SEM without exposing the sample to a reduced-pressure ambient in this way consists of preparing a sample holder (sample capsule that may or may not be hermetically sealed) whose opening (aperture) has been sealed off by a film, placing the sample in the holder, and installing the holder in an SEM sample chamber that is placed in the reduced-pressure ambient.

The inside of the sample holder in which the sample is placed is not evacuated. The film that covers the opening formed in the sample holder (sample capsule) can withstand the pressure difference between the reduced-pressure ambient inside the SEM sample chamber and the ambient (e.g., atmospheric-pressure ambient) of the inside of the sample holder that is not pumped down. Furthermore, the film permits an electron beam to pass therethrough (see JP-T-2004-515049).

When a sample is inspected, a culture medium is first put into a sample capsule together with cells. The cells are cultivated on the film. Then, the sample capsule is placed into an SEM sample chamber that is in a reduced-pressure ambient. An electron beam is directed at the sample placed within the sample capsule from outside the capsule via the film on the capsule placed in the SEM sample chamber. Backscattered electrons are produced from the irradiated sample. The backscattered electrons pass through the film on the capsule and are detected by a backscattered electron detector mounted in the SEM sample chamber. Consequently, an SEM image is derived.

However, with this technique, the sample is sealed in the closed space and so it has been impossible to give a stimulus to cells using a manipulator or pipette. The amount of the culture medium put into the sample capsule is about 15 µl. Therefore, as the culture medium evaporates, the salinity concentration rises, making it difficult to culture cells. Where the cells should be observed or inspected in vivo, there arises a problem.

This problem can be solved by increasing the size of the sample capsule to increase the capacity. However, if the film is destroyed either by a stimulation induced by an electron beam or by a mechanical stimulus, a new problem is created. That is, the inside of the apparatus is contaminated with a large amount of culture medium.

An example of a method of obtaining an SEM image by preparing a film withstanding the pressure difference between vacuum and atmospheric pressure, irradiating a sample with an electron beam via the film, and detecting backscattered electrons produced from the sample in this way is described also in "Atmospheric scanning electron microscopy," Green, Evan Drake Harriman, Ph.D., Stanford University, 1993 (especially, Chapter 1: Introduction).

Examples in which two films of the structure described above are placed opposite to each other with a sample interposed between the films and in which an image is acquired by a transmission electron microscope are described in JP-A-47-24961 and JP-A-6-318445. Especially, the latter patent document also states a case in which an SEM image of the sample interposed between such films is acquired.

JP-A-2007-292702 discloses a sample inspection apparatus equipped with an open-close valve for partitioning the space between a film and primary beam irradiation device within a vacuum chamber in order to permit the sample held on the film to be exchanged quickly and to prevent contamination inside the vacuum chamber.

The resolution of an optical microscope is not high enough to observe very tiny regions of biological cells. Imaging using SEM is required. In order to observe cells by SEM while maintaining the liquid, a sample (cells) cultured on a laboratory dish is sealed into a sample capsule. The sample is irradiated with an electron beam via the film formed on the sample capsule. Thus, the sample is imaged.

However, the sample capsule is a narrow, closed space. Therefore, there is the problem that it has been impossible to directly observe the state of the sample immediately after a stimulus is given from the outside to the sample using a manipulator or pipette. Furthermore, the capacity inside the sample capsule is small. Consequently, when moisture evaporates and the salinity concentration rises, it is difficult to culture cells for a long time inside the sample capsule. Hence, there are problems in observing cells for a long time.

JP-A-2007-292702 states that when a sample is exchanged, the space between the film and the primary beam irradiation device is partitioned off by the open-close valve and that under this condition, only the space on the film side is returned to the normal pressure. It also states that if the film is damaged during inspection of the sample, the valve is closed, partitioning off the space inside the vacuum chamber to thereby prevent contamination of the inside of the vacuum chamber.

With the open-close valve described in JP-A-2007-292702, however, the space inside the vacuum chamber is partitioned off. Therefore, it is possible to prevent contamination of the space in which the primary beam irradiation device is located, but it has been difficult to prevent contamination of the space on the film side.

SUMMARY OF THE INVENTION

It is an object of the present invention to provide an inspection method which, if a film holding a liquid sample is damaged, minimizes contamination of the whole vacuum chamber located between the film and the primary beam irradiation device with the liquid sample to thereby facilitate maintaining the inspection apparatus, thus permitting efficient imaging or inspection of the liquid sample. It is another object of the invention to provide a reagent solution for use in this inspection method.

An inspection method, according to the present invention, starts with holding a sample on a first surface of a film that covers an opening formed in a frame-like member. The sample includes a specimen to be inspected and a reagent solution holding the specimen. The sample is irradiated with a primary beam via the film from a second surface of the film. Secondary signals produced from the sample in response to the primary beam irradiation are detected. A plugging agent consisting of particles having sizes capable of plugging up at least a part of the opening is mixed in the reagent solution.

Another inspection method, according to the present invention, starts with holding a sample on a first surface of a film that covers an opening formed in a frame-like member. The sample includes a specimen to be inspected and a reagent solution holding the specimen. Then, a plugging agent consisting of particles having sizes capable of plugging up at least a part of the opening is mixed into the reagent solution. The sample is irradiated with a primary beam via the film from a second surface of the film. Secondary signals produced from the sample in response to the primary beam irradiation are detected.

The frame-like member may have a lattice structure inside the opening. Cells are formed in the lattice structure. In this case, the plugging agent consisting of particles having sizes capable of plugging up at least some of the cells of the lattice structure may be mixed into the reagent solution. The sizes of the particles of the plugging agent can be so set that the particles do not pass through the cells of the lattice structure.

The primary beam can be an electron beam or an ion beam. The secondary signals can be any one type of backscattered electrons, secondary electrons, X-rays, cathodoluminescent light, and absorption current.

According to particular embodiments, the plugging agent is made of polytetrafluoroethylene, latex, alumina, polystyrene, polymethyl methacrylate, silica, or glass. Preferably, the surface of the plugging agent is coated with a metal layer. More preferably, the density of the plugging agent is higher than the density of the liquid component of the reagent solution by a factor of 0.9 to 1.1. If the concentration of particles of the plugging agent in the reagent solution is $0.001/\mu l$ to $1/\mu l$, appropriate advantages are obtained.

The reagent solution can contain any one of water, phosphate buffer, and liquid culture medium.

The reagent solution, according to the present invention, is used to hold a specimen to be inspected when the specimen is inspected by being irradiated with a primary beam via a film that covers an opening formed in a frame-like member. A plugging agent consisting of particles having sizes capable of plugging up at least a part of the opening is mixed in the reagent solution.

Where a lattice structure having cells is mounted in the opening of the frame-like member, the sizes of the particles of the plugging agent can be so set that the particles of the plugging agent do not pass through the cells of the lattice structure.

Preferably, the maximum length of the particles of the above-described plugging agent is from 10 to 500 µm. According to particular embodiments, the plugging agent can be made of polytetrafluoroethylene, latex, alumina, polystyrene, polymethyl methacrylate, silica, or glass. The surface of the plugging agent is preferably coated with a metal layer.

Preferably, the density of the plugging agent is higher than the density of the liquid component of the reagent solution by a factor of 0.9 to 1.1. If the concentration of particles of the plugging agent in the reagent solution is $0.001/\mu l$ to $1/\mu l$, appropriate advantages are obtained.

The reagent solution can contain at least one of water, phosphate buffer, and liquid culture medium.

In the inspection method, according to the present invention, a plugging agent consisting of particles having sizes capable of plugging up at least a part of the opening in the frame-like member covered with a film for holding the sample is mixed in a reagent solution constituting the sample.

In the reagent solution, according to the present invention, a plugging agent consisting of particles having sizes capable of plugging up at least a part of the opening of the frame-like member covered with a film is mixed in the reagent solution.

In the present invention, because of these configurations, if the film holding the sample is damaged and a hole is formed in the film during inspection of a liquid sample containing a specimen to be inspected and a reagent solution, particles of the plugging agent are moved and sucked into the hole. Consequently, the hole can be plugged up with any one of the particles of the plugging agent.

Consequently, if the film is damaged, the amount of intrusion of the sample into the inspection apparatus can be reduced greatly. In the past, the inside of the apparatus (i.e., the inside of the vacuum chamber) has been required to be cleaned whenever the film becomes damaged. Adoption of the present invention makes it unnecessary to clean the apparatus even if the film is damaged ten times or more.

Accordingly, maintenance of the inspection apparatus can be alleviated and facilitated. Observation or inspection of a liquid sample can be carried out efficiently.

Other objects and features of the invention will appear in the course of the description thereof, which follows.

DESCRIPTION OF THE PREFERRED EMBODIMENTS

Inspection methods, according to the present invention, and reagent solutions used in the inspection methods are hereinafter described with reference to the drawings.

Figure 1:
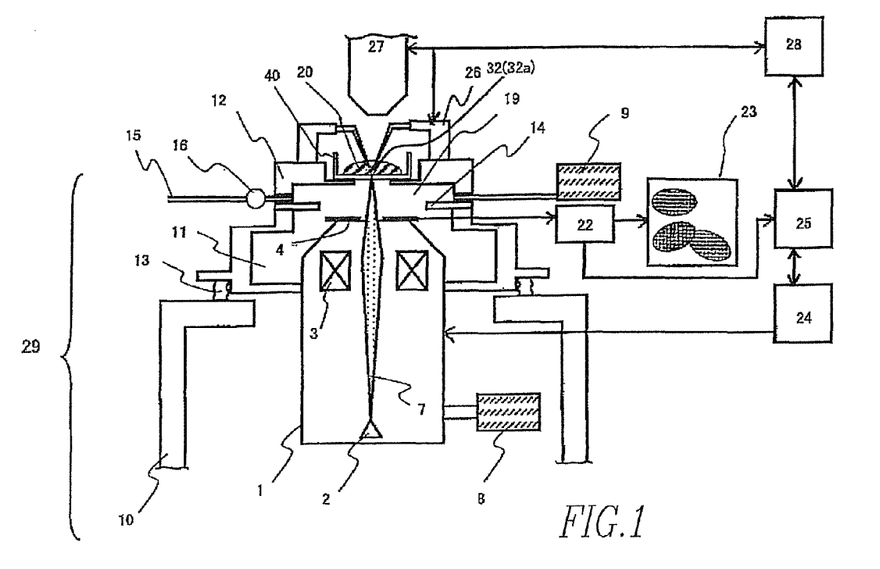
FIG. 1 is a schematic diagram of a sample inspection apparatus, according to the present invention.

FIG. 1 is a schematic diagram of a sample inspection apparatus according to the present invention. The apparatus consists chiefly of an optical microscope 27, a manipulator 26, and an electron beam apparatus section 29 located under a sample holder 40. The electron beam apparatus section 29 includes an electron optical column 1 forming the primary beam irradiation device. An electron gun 2 forming an electron source is disposed in the electron optical column 1 and emits an accelerated electron beam 7 that is a primary beam. The electron beam 7 is one kind of charged-particle beam. The beam 7 is focused by a condenser lens 3 (objective lens).

The focused electron beam 7 is directed at a liquid sample 20 via a sample-holding film 32 (described later) formed on the sample holder 40. The sample 20 is held on the sample holder 40. In the present embodiment, the liquid sample 20 includes biological cells to be inspected and a culture medium acting as a reagent solution holding the cells.

The front-end side of the electron optical column 1 is connected with a vacuum chamber 11. The electron gun 2 is mounted in the base side of the column 1. The base side of the column 1 is located under the vacuum chamber 11. Because of this configuration, the electron beam 7 released from the electron gun 2 travels upward through the column 1, passes through the space inside the vacuum chamber 11 and through the sample-holding film 32, and reaches the liquid sample 20.

During the illumination, the electron beam 7 is deflected by deflection apparatus (not shown). Thus, the electron beam 7 scans the liquid sample 20. At this time, the cells which are contained in the sample 20 and which are to be inspected are also scanned with the electron beam 7.

The electron optical column 1 forms the primary beam irradiation device in this way. In the present embodiment, the column is of the inverted type. A backscattered electron detector 4 is mounted on the front-end side of the column 1 inside the vacuum chamber 11. The backscattered electron detector 4 detects backscattered electrons produced when the specimen included in the liquid sample 20 is illuminated with the electron beam 7. For example, a semiconductor detector using a PN junction or a scintillator detector using a YAG crystal is used as the backscattered electron detector 4. The output signal from the backscattered electron detector 4 is sent to an image formation device 22 disposed outside the vacuum chamber 11.

The image formation device 22 forms image data based on the output signal from the detector 4. The image data corresponds to an SEM image, and is sent to a display device 23. The display device 23 displays an image based on the image data sent in. The displayed image forms an SEM image. If necessary, the image data formed by the image formation device 22 is sent to a computer 25. The computer 25 image-processes the image data and makes decisions based on the result of the image processing.

The inside of the electron optical column 1 is pumped down to a desired pressure by first vacuum pump 8. The inside of the vacuum chamber 11 is evacuated to a desired pressure by vacuum pump (not shown). The vacuum chamber 11 is placed over a pedestal 10 via a vibration-proofing device 13.

A sample holder placement portion 12 is formed on top of the vacuum chamber 11 and provided with a hole to permit the electron beam 7 to be directed at the sample-holding film 32. The sample holder 40 is placed on the placement portion 12 via an O-ring (not shown). Consequently, the sample holder 40 is withdrawably supported in the vacuum chamber 11.

An open-close valve 14 is mounted in the vacuum chamber 11 near its top portion and used to partition off the space 19 between the sample holder 40 and the front end of the electron optical column 1 (primary beam irradiation device) within the vacuum chamber 11.

Figure 2:
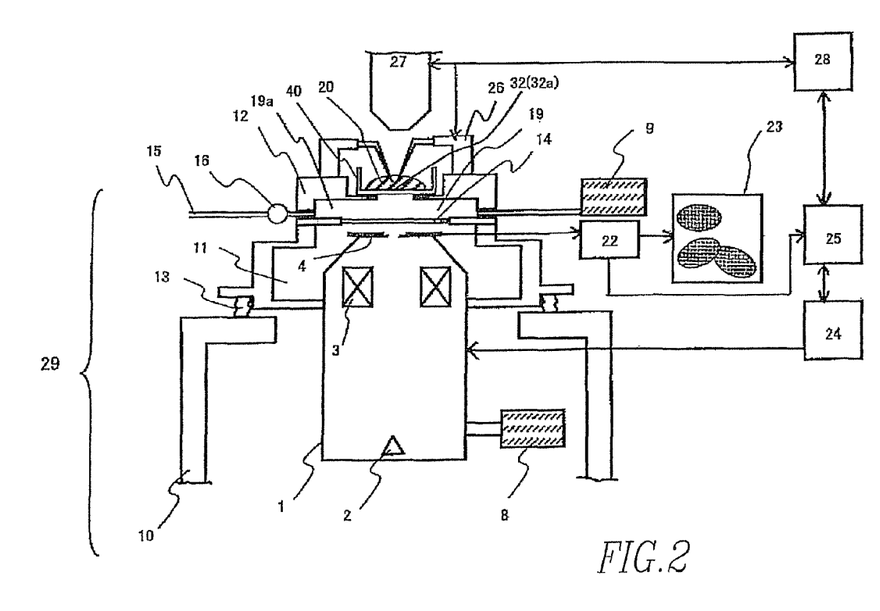
FIG. 2 is a schematic diagram similar to FIG. 1, but showing a different state.

In FIG. 1, the open-close valve 14 is opened. When the valve 14 is closed, the space 19 is partitioned off in the vacuum chamber 11 as shown in FIG. 2. When the space 19 is partitioned off by the open-close valve 14 in this way, a hermetically sealed space 19a is formed between the valve 14 and the sample-holding film 32. The space 19a is partitioned by the valve 14 on its one side and located on the side of the sample holder 40.

Second vacuum pump 9 (pressure-reducing pump) is in communication with the space 19a. The second vacuum pump 9 can evacuate the space 19a independently. A gas supply (not shown) is connected with the space 19a and supplies a gas, such as nitrogen or air, into the space 19a to return the inside of the space 19a from a pressure-reduced state to normal-pressure (atmospheric-pressure) state. In consequence, the space 19a can be returned from the reduced-pressure state to the normal-pressure state independently.

A cleaning device (not shown) is connected with the space 19a to supply a cleaning agent into the space 19a for cleaning it. As a result, the wall surface defining the space 19a is cleaned.

The used cleaning agent is a cleaning liquid consisting of at least one of a detergent, ethanol, alcohol, acetone, and aqueous hydrogen peroxide. Alternatively, vapors of these materials may be used. The cleaning agent supplied in the space 19a is discharged from it through a discharge tube 15 after the cleaning. Another open-close valve 16 is mounted in the discharge tube 15. The open-close valve 16 is opened to permit the cleaning agent to be discharged to the outside through the discharge tube 15. When an inspection (described later) of the sample is carried out, the valve 16 is closed.

The space 19a can be disinfected by irradiating the space 19a with ultraviolet radiation or other radiation.

The electron beam apparatus section 29 equipped with the electron optical column 1 and the vacuum chamber 11 is controlled by an electron beam controller 24. The manipulator 26 for giving a stimulus (such as a voltage, chemical substance, or medicine) to the specimen and for moving the specimen if necessary and an optical microscope 27 are placed on the sample holder placement portion 12. The microscope 27 permits one to observe the specimen and to check the position of the manipulator 26. These components are controlled by an overall controller 28.

The optical axis of the optical microscope 27 is coincident with the optical axis of the electron beam 7. Alternatively, the center of field of view of the optical microscope 27 is coincident with the center of the field of view of the SEM image. A region observed by the optical microscope can be made substantially coincident with the SEM image. The field of view of the SEM image and the field of view of the optical microscope 27 can be adjusted by manipulating the manipulator 26 or moving the sample holder placement portion 12 on which the sample holder 40 is placed by means of a moving mechanism (not shown).

The sample inspection apparatus, according to the present invention, has the electron beam apparatus section 29, manipulator 26, optical microscope 27, electron beam controller 24, overall controller 28, image formation device 22, and display device 23. These portions are connected with the computer 25. Information can be exchanged between these portions.

Figure 3:
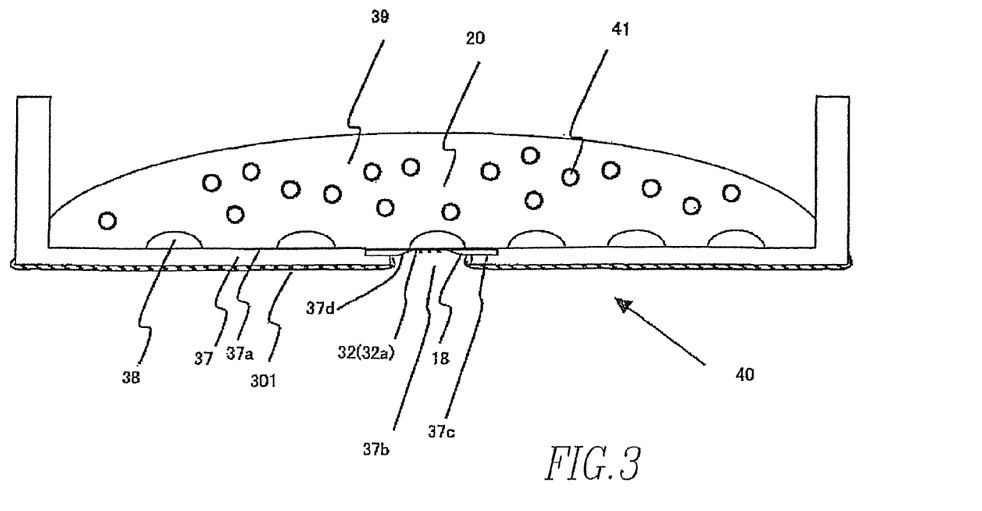
FIG. 3 is a cross-sectional view of a sample holder, according to the present invention.

The sample holder 40 is constructed as shown in FIG. 3. The sample holder 40 is composed of a dish-like body portion 37 made of plastic or glass and a film holder (frame-like member) 18 on which the sample-holding film 32 is formed. The film 32 transmits the electron beam 7. A recessed portion is formed inside the dish-like body portion 37. The bottom surface of the recessed portion forms a sample-holding surface 37a that is open.

The sample-holding surface 37a of the dish-like body portion 37 is (centrally in the example of FIG. 3) provided with a through-hole 37b. The step portion 37c is formed around the through-hole 37b on the side of the sample-holding surface 37a. The film holder 18 is disposed on the step portion 37c and has the sample-holding film 32. The sample-holding film 32 has a first surface 32a that forms the sample-holding surface 37a. The sample-holding surface 37a is substantially flush with the sample-holding surface 37a of the dish-like body portion. Consequently, at least a part of the sample-holding surface 37a of the sample holder 40 is formed by the sample-holding film 32.

Tapering portions 37d are formed on the side of the through-hole 37b on the opposite side of the sample-holding surface 37a. The tapering portions 37d are spread apart toward the surface on the opposite side of the sample-holding surface 37a. The spread angle is set to 90° to 120°.

A region of the lower surface of the sample holder 40 might be exposed to a vacuum ambient and become irradiated with the electron beam 7. A conductive film 301 is formed on this region to prevent charging of the sample holder 40 when it is irradiated with the beam 7. The conductive film 301 is in contact with the film holder 18. Electric charge accumulated by being illuminated by the electron beam 7 can be dissipated away to the liquid sample 20 via the film holder 18 made of silicon. The presence of the conductive film 301 reduces the charging of the lower surface of the sample holder 40 and can prevent displacement of the orbit of the beam 7 (that would normally be produced when the liquid sample 20 is illuminated with the beam 7) and distortion and illumination spots in the SEM image that would be normally produced by displacement of the orbit of backscattered electrons.

Accumulation of electric charge can be prevented with certainty by connecting a grounding line to the liquid sample 20 or electrically connecting the conductive film 301 with the sample holder placement portion 12. The conductive film 301 can be formed, for example, by vapor-depositing aluminum or gold or applying silver paste.

Figure 4:
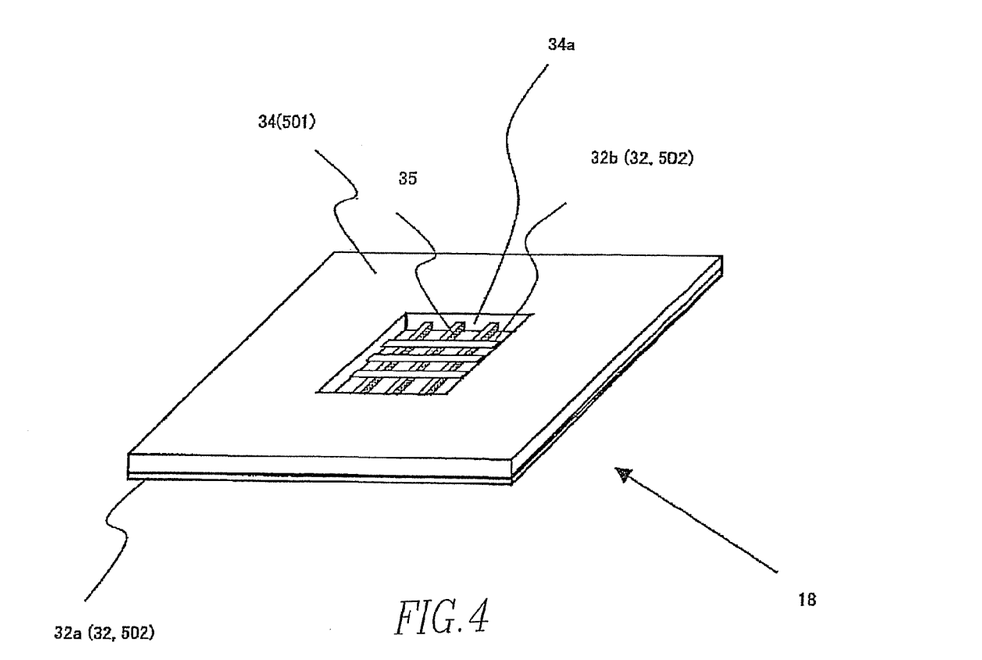
FIG. 4 is a schematic perspective view of a frame-like member constituting a frame-like member, according to the present invention.

The structure of the film holder 18 is shown in FIG. 4. The sample-holding film 32 is formed on a silicon substrate 34. A first surface 32a of the sample-holding film 32 (lower surface as viewed in FIG. 4; upper surface as viewed in FIG. 3) is exposed. The liquid sample 20 containing the reagent solution such as a culture medium and a specimen to be inspected such as cells) is placed on the first surface (sample-holding surface) 32a of the sample-holding film 32. Since the first surface 32a is under atmospheric pressure, evaporation of moisture from the liquid sample 20 can be suppressed to a minimum.

The silicon substrate 34 is centrally provided with an opening 34a (upper surface in FIG. 4; lower surface in FIGS. 1 and 3) covered with the sample-holding film 32. A central portion of the second surface 32b of the sample-holding film 32 is exposed to the inside ambient of the vacuum chamber 11 through the opening 34a. The first surface 32a of the sample-holding film 32 is exposed to the atmospheric-pressure ambient, while the second surface 32b is exposed to the vacuum ambient. In order to withstand the pressure difference, the film 32 is supported and reinforced with a lattice 35.

Figure 5:
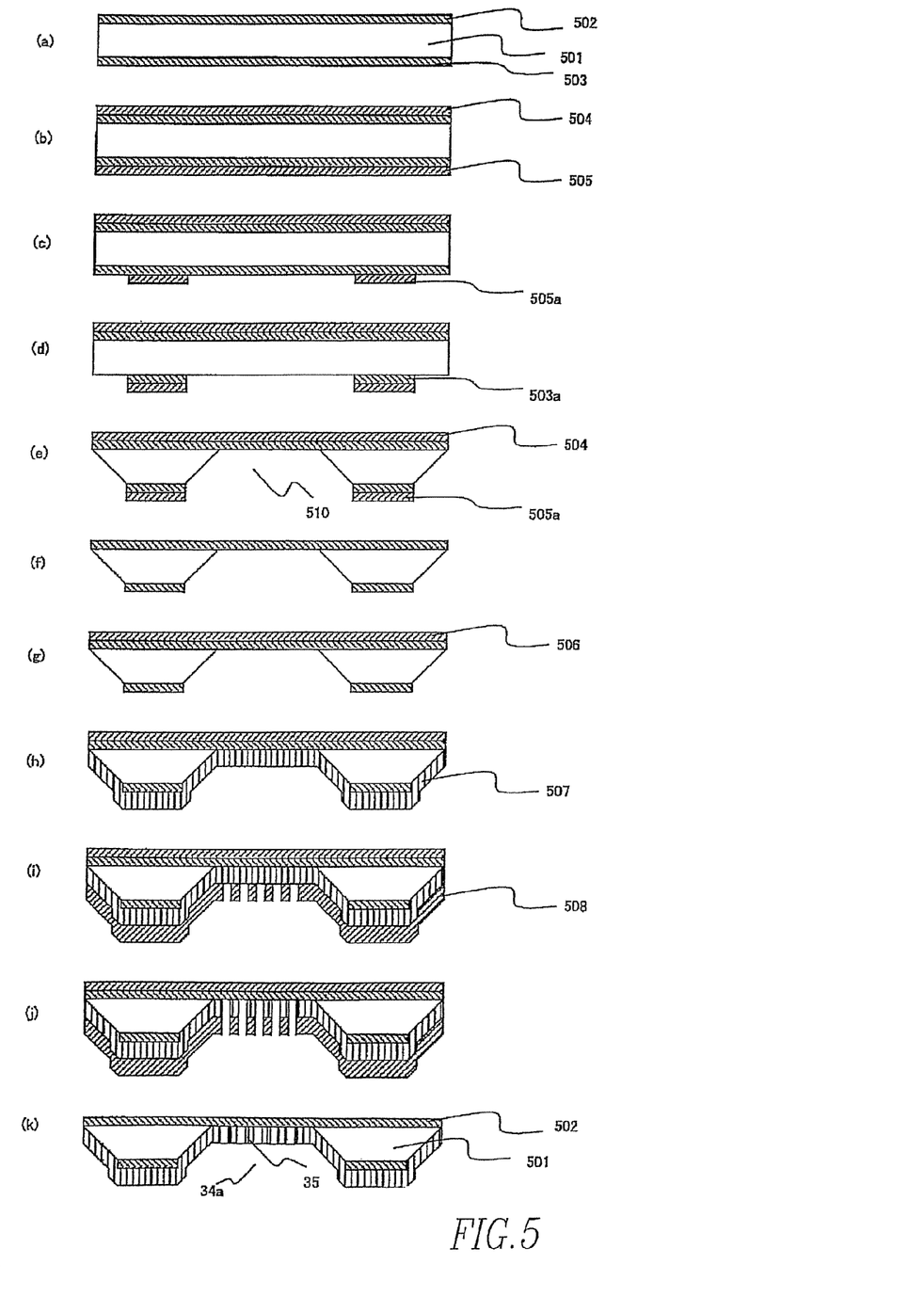
FIG. 5 shows cross sections illustrating a method of fabricating the frame-like member constituting the sample holder, according to the present invention.

A method of creating the film holder 18 is next described by referring to FIG. 5. First, as shown FIG. 5(a), silicon nitride films 502 and 503 are formed on a silicon substrate 501 using CVD (chemical vapor deposition). A typical thickness of the films 502 and 503 is 30 nm. Layers of resist 504 and 505 are applied on the silicon nitride films 502 and 503, respectively (FIG. 5(b)). The layer of resist 505 is patterned photolithographically to leave behind resist layer portions 505a (FIG. 5(c)). Using the resist pattern as a mask, the silicon nitride film 503 is processed by dry etching, and silicon nitride film portions 503a are left behind (FIG. 5(d)).

Using the pattern as a mask, the silicon substrate 501 is wet-etched with KOH to form an opening 510 (FIG. 5(e)). The resist layer portions 504 and 505a are removed by ashing (FIG. 5(f)). Where the lattice 35 is not present, the film holder 18 is completed at this point. Resist 506 is applied on the layer of silicon nitride film 502 (FIG. 5(g)). A layer of metal 507 of Al or Ni is formed to a thickness of 1 μm on the opposite side of the silicon nitride film 502 (FIG. 5(h)). Resist 508 is applied on the metal layer 507, and a pattern is photolithographically formed using a mask (FIG. 5(i)). Using the resist layer 508 as a mask, the metal layer 507 is etched (FIG. 5(j)). Finally, the resist layer 508 is removed by ashing or organic cleaning (FIG. 5(k)). As a result, the opening 34a and lattice 35 are formed.

The film holder 18 fabricated in this way is inverted up and down from the state of FIG. 4. The first surface 32a of the silicon nitride film 502 that is the sample-holding film 32 is taken as an upper surface. The second surface 32b can also be taken as an upper surface.

The film holder 18 is firmly attached to the step portion 37c over the through-hole 37b formed in the dish-like body portion 37 forming the sample holder 40. Thus, the sample holder 40 is fabricated (FIG. 3). To attach the film holder 18 to the step portion, bonding using an epoxy-based or silicone-based adhesive or fusion making use of heat, ultrasonic waves, or laser can be used. Consequently, the film holder 18 is firmly held in a position corresponding to the through-hole 37b in the sample-holding surface 37a of the dish-like body portion 37.

In the present embodiment, the dish-like body portion 37 and film holder 18 are combined to fabricate the sample holder 40. The sample-holding film 32 may be directly firmly bonded to the dish-like body portion 37. The dish-like body portion 37 and the sample-holding film 32 may be fabricated integrally. Furthermore, cell adhesion molecules (described later) acting as molecules for bonding the sample may be applied to the sample-holding surface 37a including the first surface 32a of the sample-holding film 32.

The thickness of the silicon nitride film 502 is set to a range of from 10 to 1,000 nm. The sample-holding film 32 of the film holder 18 is made of silicon nitride. In addition, the film 32 may be made of silicon oxide, boron nitride, polymer, polyethylene, polyimide, polypropylene, or carbon. Where films of these materials are used, their film thicknesses are set to a range of from 10 to 1,000 nm. The sample-holding film 32 made of the aforementioned material transmits the electron beam 7 but does not transmit gas or liquid. Moreover, it is necessary that the film be capable of withstanding a pressure difference of at least 1 atmosphere across the opposite surfaces.

As the thickness of the sample-holding film 32 is reduced, scattering of the electron beam 7 is reduced and, therefore, the resolution is improved but the film is more easily damaged. As the thickness is increased, scattering of the electron beam 7 increases, resulting in decreased resolution. However, the film is less likely to be damaged. The preferable thickness of the film is 20 to 200 nm.

An inspection method, according to the present invention, is next described by referring to FIGS. 1, 2, 3, and 4. First, as shown in FIG. 3, cells 38 (sample cells) to be inspected are cultured within a culture medium 39 (reagent solution) using the sample holder 40. A plugging agent 41, for example, made of polystyrene balls, is put in the culture medium. The polystyrene balls are so large that they cannot pass through the cells in the lattice 35. In order to culture the sample cells 38 as shown in FIG. 3, it is necessary to graft the sample cells from the laboratory dish where they have been previously cultured to the sample holder 40. For this purpose, a normal method as described below is used.

The culture medium is Product No. D5796 of Sigma-Aldrich Co., for example. First, the culture medium is discarded from the laboratory dish where the cells have been previously cultured. A mixture liquid of trypsin and EDTA (ethylenediaminetetraacetic acid) is put into the dish to peel off the cells adsorbed to the dish. The peeled cells are recovered into a centrifuge tube. A culture medium is put into the tube. The trypsin is inactivated and then the cells are spun down. Then, the supernatant fluid is discarded from the centrifuge tube and the remaining liquid is stirred in the culture medium. A part (e.g., 1/10) of the stirred liquid including the cells 38 is entered into the sample holder 40. The reagent solution (culture medium) 39 is grafted. Under this condition, the holder is allowed to stand still in a cell culture chamber. After a lapse of several hours, the cells 38 begin to be adsorbed onto the sample-holding surface 37a of the sample holder 40 including the first surface 32a of the sample-holding film 32 and proliferate. The aforementioned method may be modified according to cells, and is merely one example. Consequently, the cells 38 to be observed or inspected are cultured within the sample holder 40. It follows that the liquid sample 20 containing the cultured cells 38 and reagent solution (culture medium) 39 is constituted.

Depending on biological cells, if cell adhesion molecules are applied to the sample-holding surface 37a of the sample holder 40 (especially, the first surface 32a of the sample-holding film 32 observed with an electron beam), cultivation is facilitated. The cell adhesion molecules cause cells arranged for cultivation and cells proliferated by cultivation to be adsorbed onto the sample-holding surface. Examples of the cell adhesion molecules include collagen, fibronectin, vitronetin, cadherin, integrin, claudins, desmogleins, neuroligin, neurexin, selectin, laminins, and poly-L-lysine.

After the cells are cultured within the sample holder 40 as described above, the sample holder 40 is placed on the holder placement portion 12. At this time, the open-close valve 14 is closed and in the state of FIG. 2. The space 19a hermetically sealed between the valve 14 and the sample-holding film 32 is at a normal pressure, or in an atmospheric-pressure ambient. Within the vacuum chamber 11, the space located under the valve 14 is in a given vacuum state (reduced-pressure state).

The inside of the electron optical column 1 in communication with this space is evacuated to a desired vacuum state by the first vacuum pump 8. The pressure (degree of vacuum) inside the vacuum chamber 11 is set to about $10^{-3}$ to $10^{-4}$ Pa, for example. The pressure (degree of vacuum) inside the electron optical column 1 (especially, around the electron gun 2) is set to about $10^{-4}$ to $10^{-5}$ Pa, for example.

Under this condition, the space 19a is reduced in pressure down to a vacuum using the second vacuum pump 9. At this time, to prevent the sample-holding film 32 from being damaged due to rapid pressure variations from the atmospheric-pressure state, the pressure is reduced from 1 atm. (101325 Pa), that is, the atmospheric pressure down to about ½ to 1/10 atm. (50 kPa to 10 kPa), using a needle valve (not shown), in a time from 1 second to 100 seconds. During this process step, it is observed that the sample-holding film 32 of the specimen holder 40 is not destroyed.

After checking that the sample-holding film 32 has not been destroyed by the above-described step, the positions of the sample cells 38 and of the manipulator 26 are checked with the optical microscope 27. A glass microtube holding microelectrodes therein is installed at the front end of the manipulator 26. A voltage can be applied to the cells through the microelectrodes. A liquid can be made to flow in and out through the glass microtube.

Under this condition, the manipulator 26 is moved while making an observation with the optical microscope 27 to bring the cells 38 close to the glass microtube. Then, a negative pressure is applied to the glass microtube to bring it into intimate contact with the cell membranes. As a result, potential response can be measured.

Figure 6:
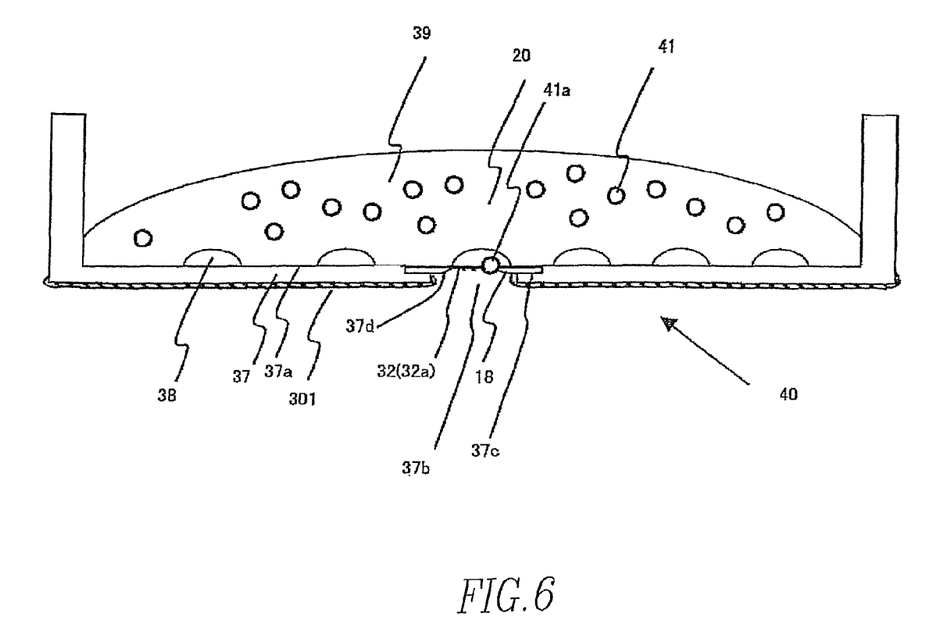
FIG. 6 is a cross-sectional view similar to FIG. 3, but in which a hole created by destruction of the frame-like member has been plugged up with a plugging agent.

When the manipulator 26 is moved as described above, if the sample-holding film 32 is erroneously damaged, contamination due to diffusion of the liquid sample 20 is restricted to within the space 19a because the open-close valve 14 is closed. Because particles of the plugging agent 41 that are so large that they cannot pass through the cells formed by the frames of the lattice 35 are put in the liquid sample 20, one particle 41a of the plugging agent 41 is adsorbed into the damaged portion as shown in FIG. 6. Consequently, the damaged portion can be plugged up.

Because the particle 41a of the plugging agent 41 cannot pass through the cells formed by the frames of the lattice 35, if an external force is applied due to a pressure difference, the particle 41a of the plugging agent 41 does not intrude into the vacuum chamber 11.

Even where the plugging agent 41 partially plugs up the hole in the damaged portion, the liquid that has flowed in expands adiabatically in a vacuum and thus the temperature drops. The liquid is solidified, thus completely plugging up the hole. Consequently, the inflow of the culture medium into the apparatus can be reduced.

If the density of the particles of the plugging agent in the liquid sample 20 is set to 0.001/µl to 1/µl, the plugging agent will create no hindrance when cells are observed. Furthermore, the amount of the liquid sample 20 flowing into the space 19a can be reduced. The plugging agent can be particulate plugging material, such as polytetrafluoroethylene, latex, alumina, polystyrene, polymethyl methacrylate, silica, or glass. The particles can assume a ball-like form. More preferably, the density of the plugging agent is higher than the density of the liquid sample by a factor of 0.9 to 1.1.

Preferably, the surface of the plugging agent is coated with a layer of a metal, such as aluminum or gold. The metal layer can be formed on the surface of the plugging agent by a vacuum deposition technique. Where the surface of the plugging agent is coated with the metal layer, if the plugging agent is illuminated with an electron beam, charging of the plugging agent can be prevented. Consequently, when the sample is illuminated with an electron beam, charging of the plugging agent can be prevented; otherwise, charged particles of the plugging agent would move to the illuminated region, hindering observation of the sample. Hence, good observation of the sample can be made.

Where no plugging agent is used, all the liquid sample 20 flows into the apparatus. Therefore, whenever the sample-holding film 32 is destroyed, the apparatus needs to be cleaned. At times, the apparatus is made unusable. In the present invention using a plugging agent, the amount of liquid that flows in is reduced. Where the open-close valve 14 is opened or where the valve 14 is not present, the apparatus can continue to be used without problem even if ten such contaminations occur.

Even where such a plugging agent is used, if the sample-holding film 32 is destroyed tens of times, the inside of the space 19a may be contaminated by diffusion of the liquid sample 20, deteriorating the performance of the electron beam apparatus section 29. In this case, the space 19a can be cleaned as mentioned previously. Where cleaning is done, the amount of the liquid sample 20 flowing in is small and so the cleaning can be carried out easily. The liquid detergent or vapor used for the cleaning can be discarded via the discharge tube 15 by opening the open-close valve 16. It is possible to make the space 19a less susceptible to contamination by coating the wall surface forming the space 19a with boron nitride or fluororesin.

We now return to the observation sequence. When the space 19a is in a reduced-pressure state or a vacuum state, it is checked that the sample-holding film 32 on which the sample 20 is placed is not destroyed. Then, the open-close valve 14 is opened. Thus, the space inside the vacuum chamber 11 is ceased to be partitioned to place the space located under the vacuum chamber 11 into communication with the space 19a. Thereafter, in order to prevent light from entering the backscattered electron detector 4 via the sample-holding film 32, the light illumination of the optical microscope 27 is ceased. Other extraneous light is blocked in a manner not shown. The blocking also shields the film holder 18 and liquid sample 20 against radiation rays produced when the electron beam 7 hits the film holder 18 and sample 20.

Then, as shown in FIG. 1, the electron beam 7 is directed at the liquid sample 20 including the cells 38 from the electron optical column 1 to perform imaging. The beam 7 passes through the sample-holding film 32 of the sample holder 40 and hits the cells 38. Backscattered electrons produced from the cells 38 in response to the illumination are detected by the backscattered electron detector 4.

Since the aforementioned tapering portions 37d are formed around the through-hole 37b of the dish-like body portion 37 forming the sample holder 40, collision of the backscattered electrons against the inner side surface of the through-hole 37b can be suppressed to a minimum. That is, the backscattered electrons can be suppressed from being blocked. The backscattered electrons can be detected efficiently by the backscattered electron detector 4.

A detection signal produced from the backscattered electron detector 4 is fed to the image formation device 22, which, in turn, forms image data based on the detection signal. Based on the image data, an image (SEM image) is displayed on the display device 23.

Subsequently, an electrical stimulus is given to the cells 38 using the microelectrodes installed at the front end of the manipulator 26. An SEM image is acquired in the same way as in the above-described process step. The response of the cells 38 to the stimulus is checked.

After the imaging, the open-close valve 14 is closed to prevent contamination of the electron optical column 1 if the sample-holding film 32 should be destroyed. Before a variation caused by application of a stimulus to the cells 38 is observed by SEM as described above, an observation may be made with the optical microscope 27. Also, at this time, if the open-close valve 14 is closed, risk of contamination occurring when the sample-holding film 32 is broken can be reduced. In any case, if the open-close valve 14 is closed when the electron beam 7 is not directed at the liquid sample 20, the probability of contamination of the inside of the apparatus can be reduced by shortening the interval for which the open-close valve 14 is opened during inspection.

Where the speed of reaction of the cells 38 to the stimulus is low, the open-close valve 14 may be once closed. The valve 14 may be again opened at a time when a reaction is deemed to have taken place. Then, imaging may be performed using the electron beam 7. The reaction can be checked with the optical microscope 27.

The manipulator 26 can have a mechanism capable of spraying a chemical substance or medicine into the liquid sample 20. Behavior of the cells 38 in response to the chemical substance or medicine can be observed or inspected while observing the cells by SEM. Furthermore, a function of permitting a liquid to flow out can be imparted to the manipulator 26. This permits the sprayed substance to be recovered. Also, the pH of the culture medium and the osmotic pressure can be maintained constant.

In the foregoing, backscattered electrons are used to form an image. Backscattered electrons produce a signal intensity proportional to the atomic number. Therefore, where the specimen is almost totally made of substances of low atomic numbers, such as a biological specimen, the image contrast is very low, and it is difficult to improve the resolution.

Accordingly, a heavy metal, such as gold, may be adsorbed onto portions of the cells 38 to be noticed in their behavior. In particular, gold is adsorbed onto the portions (antigen) via an antibody by causing the antigen tagged with gold particles having the nature of being adsorbed on the portions (antigen) to be sprayed against the cells by making use of an antigen-antibody reaction. Furthermore, a fluorescent dye or quantum dots (e.g., nanoparticles of Si or particles of CdSe coated with ZnS and having sizes of 10 to 20 nm) that emit light when irradiated with an electron beam may be previously adsorbed onto certain portions of the cells 38, and the emitted light may be observed with an optical microscope.

In the above embodiment, normally used gold particles have particle diameters of 10 to 30 nm. However, the adsorptive force between the antibody and gold particles is weak, and gold particles of 10 to 30 nm may not be attached. In this case, very small gold particles (nanogold particles) having particle diameters on the order of nanometers are first attached to the antibody. Under this condition, the gold particles are too small and it is difficult to observe them by SEM. Silver is adsorbed around the gold particles by making use of a silver sensitizer. This makes it easier to detect them by SEM.

In the foregoing, cells previously cultured in a laboratory dish are taken out and grafted onto the sample holder 40. Then, the cells are cultured. Alternatively, cells may be taken from a living organism and directly placed on the sample-holding surface 37a of the sample holder 40. The cells may be cultured in the sample holder 40.

As described so far, the present invention makes it possible to observe or inspect a specimen via the sample-holding film 32, the specimen being included in a liquid and to be inspected. Especially, the use of an open sample chamber facilitates giving a stimulus to cells because access to the sample can be made from the outside. Furthermore, the amount of culture medium can be increased. Cells are allowed to survive for a long time.

Where the sample-holding film 32 is broken, liquid flows into the apparatus through the torn gap. The plugging agent 41 consisting of particles having sizes capable of plugging up the gap is mixed in the liquid. The plugging agent 41 can plug up at least a part of the gap. Consequently, the amount of liquid flowing into the apparatus can be reduced. This makes it unnecessary to clean the inside of the apparatus if the sample-holding film 32 is destroyed ten times. In addition, if the inside is cleaned, the amount of adhered contaminants is small. Hence, the cleaning can be done easily. In this way, the present invention enhances convenience in use of the apparatus.

In the above embodiment, the plugging agent is made of polystyrene. The plugging agent may also be made of other substances, such as polytetrafluoroethylene, latex, alumina, polymethyl methacrylate, silica, or glass. Where the density of the plugging agent is higher than the density of the liquid sample by a factor of 0.9 to 1.1 (more preferably 1.0 to 1.1), the plugging agent is suspended or settled in the liquid. If the sample-holding film is destroyed, the torn gap can be quickly plugged up. If the plugging agent is too heavy, it takes a long time to move the plugging agent. If the plugging agent is too light, it is impossible to plug up the gap until the liquid is fully eliminated. Therefore, it is important to appropriately set the density.

Where the concentration of particles of the plugging agent relative to the liquid sample is $0.001/\mu l$ to $1/\mu l$, the observation is not hindered. The plugging agent is mixed, for example, in water, culture medium, or phosphate buffer, thus preparing a reagent for testing. It is expected that the aforementioned advantages can be obtained by adding the testing reagent to a liquid sample before observation.

Furthermore, in the present invention, the inverted type SEM is used. Depending on samples, a normal non-inverted type SEM using a sealed sample capsule as described in the "Description of the Related Art" of this specification can be used without problem. In this case, however, the density of the plugging agent is preferably higher than the density of liquid sample by a factor of 0.9 to 1.0.

The sample cells 38 cultured on the sample holder 40 are observed through the cells in the lattice 35. Biological cells have sizes of 10 to hundreds of micrometers. The lattice spacing that provides easy observation as estimated from the sizes of sample cells is 10 to 500 µm. Therefore, if the maximum length of particles of the plugging agent is set according to the lattice interval, i.e., 10 to 500 µm, the born gap in the sample-holding film 32 can be plugged up efficiently.

In the above embodiments, an electron beam is used as the primary beam. If the sample-holding film 32 shows sufficient shock resistance and strength against impingement of other charged-particle beams, such as a helium ion beam, the invention can also be applied in a case where the other charged-particle beam is used.

In the above embodiments, backscattered electrons are used as a secondary signal. Information about the cells 38 can also be obtained by detecting other forms of information, such as secondary electrons, X-rays, cathodoluminescent light, and electric current absorbed into the cells 38 to be inspected. It is convenient to use the manipulator 26 in measuring the absorption current.

It is required that the sample-holding film 32 of the present embodiment withstand a pressure difference of at 1 atm. and that gas or liquid do not flow in or out. Specifically, the material of the film 32 includes at least one of polymer, polyethylene, polyimide, polypropylene, carbon, silicon oxide, silicon nitride, and boron nitride.

As described previously in the inspection method, according to the present invention, the sample 20 containing the specimen 38, such as cells to be inspected, and reagent solution 39 holding the specimen 38 is held on the first surface of the film 32 that covers the opening in the film holder 18. A primary beam is directed at the sample 20 from the second surface 32b of the film 32 via the film 32. A secondary signal produced from the sample 20 in response to the primary beam irradiation is detected. In this inspection method, the plugging agent 41 consisting of particles having sizes capable of plugging up at least a part of the opening 34a is mixed in the reagent solution 39.

The inspection method, according to the present invention, comprises the steps of: holding the sample 20 on the first surface 32a of the film 32 disposed on the film holder 18 having the opening 34a, the opening 34a of the film holder 18 being covered with the film 32, the sample 20 containing the specimen 38 to be inspected, and the reagent solution 39 holding the specimen 38; mixing the plugging agent 41 consisting of particles having sizes capable of plugging up at least a part of the opening 34a into the reagent solution 39; directing a primary beam at the sample 20 via the film 32 from the second surface of the film 32; and detecting a secondary signal produced from the sample 20 in response to the primary beam irradiation.

The film holder 18 has a lattice structure inside the opening 34a. The particles of the plugging agent 41 can plug up at least some of the cells in the lattice structure. The particles of the plugging agent 41 can have sizes not passing through the cells inside the lattice structure.

The primary beam can be an electron beam or an ion beam. The secondary signal can be any one type of backscattered electrons, secondary electrons, X-rays, cathodoluminescent light, and absorption current. The first surface 32a of the film 32 can be taken as an upper surface and the second surface 32b of the film 32 can be taken as a lower surface.

The reagent solution, according to the present invention, is used to hold the specimen 38 when it is inspected by irradiating it with a primary beam via the film 32 that covers the opening 34a in the frame-like member 18. The plugging agent 41 consisting of particles having sizes capable of plugging up at least a part of the opening 34a is mixed in the reagent solution.

Where a lattice structure is formed inside the opening 34a of the frame-like member 18, the sizes of the particles of the plugging agent 41 can be so set that the particles do not pass through cells in the lattice structure.

The maximum length of the particles of the plugging agent 41 described above can be set to a range of 10 µm to 500 µm.

The plugging agent 41 can be made of polytetrafluoroethylene, latex, alumina, polystyrene, polymethyl methacrylate, silica, or glass.

The surface of the plugging agent 41 can be coated with a metal layer.

The density of the plugging agent 41 can be set higher than the density of the liquid component of the reagent solution 39 by a factor of 0.9 to 1.1. The concentration of particles of the plugging agent 41 in the reagent solution 39 can be set to a range of $0.001/\mu l$ to $1/\mu l$.

The reagent solution 39 can contain at least any one of water, phosphate buffer, and liquid culture medium.

Having thus described our invention with the detail and particularity required by the Patent Laws, what is desired protected by Letters Patent is set forth in the following claims.

The invention claimed is:

1. An inspection method comprising the steps of:
   preparing a sample containing a specimen to be inspected and a reagent solution holding the specimen therein;
   holding the sample on a first surface of a film disposed on a frame-like member having an opening, the opening of the frame-like member being covered with the film;
   irradiating the sample with a primary beam via the film from a second surface of the film; and
   detecting a secondary signal produced from the sample in response to the primary beam irradiation,
   wherein a plugging agent consisting of particles having sizes capable of plugging up at least a part of the opening is mixed in the reagent solution.

2. An inspection method comprising the steps of:
   preparing a sample containing a specimen to be inspected and a reagent solution holding the specimen therein;
   holding the sample on a first surface of a film disposed on a frame-like member having an opening, the opening of the frame-like member being covered with the film;
   mixing a plugging agent consisting of particles having sizes capable of plugging up at least a part of the opening into the reagent solution;
   irradiating the sample with a primary beam via the film from a second surface of the film; and
   detecting a secondary signal produced from the sample in response to the primary beam irradiation.

3. An inspection method as set forth in claim 1 or 2, wherein a lattice structure is formed inside the opening of the frame-like member, and wherein the particles of the plugging agent can plug up at least some of cells inside the lattice structure.

4. An inspection method as set forth in claim 3, wherein the particles of the plugging agent have sizes not passing through the cells inside the lattice structure.

5. An inspection method as set forth in claim 1 or 2, wherein said primary beam is an electron beam or an ion beam, and wherein said secondary signal is any one type of backscattered electrons, secondary electrons, X-rays, cathodoluminescent light, and absorption current.

6. An inspection method as set forth in claim 1 or 2, wherein the first surface of said film forms an upper surface, while the second surface of the film forms a lower surface.

7. An inspection method as set forth in claim 1 or 2, wherein said plugging agent is made of any one of polytetrafluoroethylene, latex, alumina, polystyrene, polymethyl methacrylate, silica, and glass.

8. An inspection method as set forth in claim 7, wherein said plugging agent is coated on its surface with a metal layer.

9. An inspection method as set forth in claim 1 or 2, wherein said plugging agent has a density that is higher than the density of liquid component of said reagent solution by a factor of 0.9 to 1.1.

10. An inspection method as set forth in claim 1 or 2, wherein within said reagent solution, the particles of the plugging agent have a concentration of $0.001/\mu l$ to $1/\mu l$.

11. An inspection method as set forth in claim 1 or 2, wherein said reagent solution includes at least any one of water, phosphate buffer, and liquid culture medium.

* * * * *